United States Patent
Kim et al.

(10) Patent No.: US 11,730,850 B2
(45) Date of Patent: Aug. 22, 2023

(54) INDOOR AIR CLEANING DEVICE FOR VEHICLE USING NON-THERMAL PLASMA AND AN OPERATION METHOD THEREOF

(71) Applicant: KYUNGPOOK NATIONAL UNIVERSITY INDUSTRY-ACADEMIC COOPERATION FOUNDATION, Daegu (KR)

(72) Inventors: Jingyu Kim, Daegu (KR); Jaeseung Jeong, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 191 days.

(21) Appl. No.: 17/393,173

(22) Filed: Aug. 3, 2021

(65) Prior Publication Data

US 2021/0379236 A1    Dec. 9, 2021

Related U.S. Application Data

(63) Continuation of application No. 15/781,317, filed as application No. PCT/KR2016/014131 on Dec. 2, 2016, now abandoned.

(30) Foreign Application Priority Data

Dec. 3, 2015    (KR) .................. 10-2015-0171584

(51) Int. Cl.
*A61L 9/22*    (2006.01)
*H01T 23/00*   (2006.01)
(Continued)

(52) U.S. Cl.
CPC ............. *A61L 9/22* (2013.01); *A61L 9/046* (2013.01); *B60H 3/0078* (2013.01); *B60H 3/06* (2013.01);
(Continued)

(58) Field of Classification Search
CPC ........ A61L 9/22; A61L 9/046; A61L 2209/16; A61L 2209/212; A61L 2209/14;
(Continued)

(56) References Cited

U.S. PATENT DOCUMENTS 3,930,815 A    1/1976  Masuda
4,978,372 A    12/1990 Pick
(Continued)

FOREIGN PATENT DOCUMENTS

JP    H11-221489 A   *  2/1998  ............. A61L 9/015
JP    10-236154 A       9/1998
(Continued)

*Primary Examiner* — Maris R Kessel
*Assistant Examiner* — Brendan A Hensel
(74) *Attorney, Agent, or Firm* — Bridgeway IP Law Group, PLLC; Sang Ho Lee; Hyun Woo Shin

(57) ABSTRACT

Provided is an indoor air cleaning device for a vehicle using a nonthermal plasma and an operation method thereof, and more particularly, to an indoor air cleaning device for a vehicle using a nonthermal plasma, in which ozone is generated by a nonthermal plasma through corona discharge and an air purifying filter is sterilized through strong oxidization action of ozone, achieving more hygienic and continuous management, static electricity of an electrostatic filter is recharged with the controlled magnitude of applied voltage to maintain the best purification performance of the filter, and negative ions beneficial for human body are generated, creating pleasant indoor air conditions.

6 Claims, 2 Drawing Sheets

(51) Int. Cl.
    *H01T 19/04* (2006.01)
    *B60H 3/06* (2006.01)
    *A61L 9/04* (2006.01)
    *B60H 3/00* (2006.01)
    *H01T 19/00* (2006.01)

(52) U.S. Cl.
    CPC ............. *H01T 19/00* (2013.01); *H01T 19/04* (2013.01); *H01T 23/00* (2013.01); *A61L 2209/11* (2013.01); *A61L 2209/14* (2013.01); *A61L 2209/16* (2013.01); *A61L 2209/212* (2013.01)

(58) Field of Classification Search
    CPC ..... A61L 2209/11; H01T 19/00; H01T 23/00; H01T 19/04; B60H 3/0078; B60H 3/06
    See application file for complete search history.

(56) References Cited

U.S. PATENT DOCUMENTS

| | | | |
|---|---|---|---|
| 7,025,806 | B2 | 4/2006 | Coppom et al. |
| 7,959,869 | B2 | 6/2011 | Taylor |
| 2013/0022503 | A1 | 1/2013 | Matsubara |
| 2013/0071298 | A1* | 3/2013 | Tanimura ................. B03C 3/02 |
| | | | 422/187 |
| 2015/0137677 | A1 | 5/2015 | Sohn |
| 2016/0118787 | A1 | 4/2016 | Ran et al. |

FOREIGN PATENT DOCUMENTS

| | | | | |
|---|---|---|---|---|
| JP | 2003-039944 A | | 2/2003 | |
| JP | 2008-036168 A | | 2/2008 | |
| KR | 100404862 | * | 11/2004 | ............... B03C 3/32 |
| KR | 10-0606427 B1 | | 7/2006 | |
| KR | 10-2013-0072098 A | | 7/2013 | |

* cited by examiner

INDOOR AIR CLEANING DEVICE FOR VEHICLE USING NON-THERMAL PLASMA AND AN OPERATION METHOD THEREOF

CROSS-REFERENCE TO RELATED APPLICATION

This application is a continuation application of the U.S. application Ser. No. 15/781,317 filed on Jun. 4, 2018, which is a National Stage Application under 35 USC § 371 of the International Application No. PCT/KR2016/014131 filed on Dec. 2, 2016, which claims priority to the Korean Patent Application No. 10-2015-0171584 filed on Dec. 3, 2015, and the disclosures of the above-identified applications are incorporated herein by reference.

TECHNICAL FIELD

The present disclosure relates to an indoor air cleaning device for a vehicle using a nonthermal plasma, and more particularly, to an indoor air cleaning device for a vehicle using a nonthermal plasma, in which ozone is generated by a nonthermal plasma through corona discharge and an air purifying filter is sterilized through strong oxidization action of ozone, achieving more hygienic and continuous management, static electricity of the electrostatic filter is recharged with the controlled magnitude of applied voltage to maintain the best purification performance of the filter, and negative ions beneficial for human body are generated, creating pleasant indoor air conditions.

BACKGROUND ART

Today people spend most of their time indoors and thus are greatly interested in indoor air pollution and purification. Factors that cause indoor air pollution may be classified into inside pollution factors such as molds, floating dust, asbestos and various microorganisms and outside pollution factors such as fine dust and yellow dust. An amount of hydrocarbon and carbon dioxide present especially in the inside, of the vehicle is 2 to 10 times higher than those measured on the roads outside of the vehicle, and air pollution is more serious during commute times when many vehicles are on the roads.

The pollution inside the vehicle may be caused by outside source pollution factors such as harmful exhaust gas NOx generated by surrounding vehicles, particulate matter (PM), CO, SOx and HC, and when these materials enter the vehicle, they may harm the driver's health and reduce the concentration level while driving, and eventually, causing accidents. In addition, inside pollution factors are caused by microbial materials living in the air conditioner or fibers, tobacco smoke, air freshener, and carbon dioxide released through breathing of the driver or passenger.

In many cases, since most of drivers drive in internal circulation mode of the ventilation system with their windows closed to prevent exhaust gas generated from surrounding vehicles from inside pollution phenomena as described above may be a more serious issue and its consequential damage to the driver may be greater.

To solve this indoor pollution problem, the most common method used is an air cleaning device. An air cleaning device usually uses an electrostatic filter as a filter for air purification. However, when the electrostatic filter is used for a long term, there is an increasing likelihood that many bacteria will grow in the filter and air passages due to humidity and accumulated impurities, the polluted air also will likely be discharged out of the air cleaning device.

Additionally, when the electrostatic filter is exposed to the outside for a long term, the surface area of the filter is reduced due to a reduction of static charge electrically charged in the filter and agglomeration phenomena of the filter fibers, and accordingly, the filter effect is drastically reduced. Therefore, in order to maintain the performance of the air cleaning device, it is necessary to periodically replace the filter.

DISCLOSURE

Technical Problem

The present disclosure is designed to solve the problems described above, and therefore the present disclosure is directed to provide an indoor air cleaning device for a vehicle using a nonthermal plasma, in which ozone is generated by a nonthermal plasma through corona discharge and an air purifying filter is sterilized through strong oxidizing action of ozone, achieving more hygienic and continuous management.

The present disclosure is further directed to provide an indoor air cleaning device for a vehicle using a nonthermal plasma, in which an air purifying filter is efficiently sterilized in combination with a corona discharge method of simple structure, static electricity of an electrostatic filter is recharged with the controlled magnitude of applied voltage to maintain the best purification performance of the filter, and negative ions beneficial for human body are generated, creating a pleasant indoor air condition.

Technical Solution

To achieve the above-described object, according to an aspect of the present disclosure, there is provided an indoor air cleaning device for a vehicle using a nonthermal plasma, installed inside the vehicle to keep air clean, including an air inlet unit in which when the air is introduced, a filter unit purifies the air, a discharge electrode unit is formed on a front surface of the filter unit, an inductive electrode unit formed on a rear surface of the filter unit, an air outlet unit through which the air purified by the filter unit is discharged to inside the vehicle, and a power control unit which applies voltage to the discharge electrode unit and the inductive electrode unit, wherein ozone is generated through discharge by the discharge electrode unit and the inductive electrode unit, and sterilizes the filter unit.

Additionally, the discharge by the discharge electrode unit and the inductive electrode unit is preferably a corona discharge, electrodes of the discharge electrode unit and the inductive electrode unit are made of stainless steel, the discharge electrode unit includes one or more wire electrodes, the discharge electrode unit preferably includes a maximum of seven wire electrodes, the inductive electrode unit includes a mesh electrode, and, the discharge electrode unit and the inductive electrode unit may be formed at a spacing of 22 to 26 mm in this instance.

Additionally, the power control unit allows a user to adjust the magnitude of voltage applied to the discharge electrode unit and the inductive electrode unit, and operation may be performed stepwise in an electrostatic charging mode, a negative ion generation mode and an ozone sterilization mode according to the magnitude of voltage adjusted by the power control unit. To this end, a mode selection button is preferably provided to allow a user to adjust the magnitude of voltage.

Advantageous Effects

According to the present disclosure described above, there is an effect in more hygienic and continuous management of the filter of the indoor air cleaning device for a vehicle by sterilizing the air purifying filter through strong oxidizing action of ozone. Additionally, there is an effect for efficient sterilization of the air purifying filter at reduced production costs in combination with the corona discharge method of simple structure, and extension of the replacement cycle of the filter to the maximum length, with consequential cost reduction by recharging static electricity of the electrostatic filter to maintain the best purification performance of the filter.

BEST MODE

Figure 1:
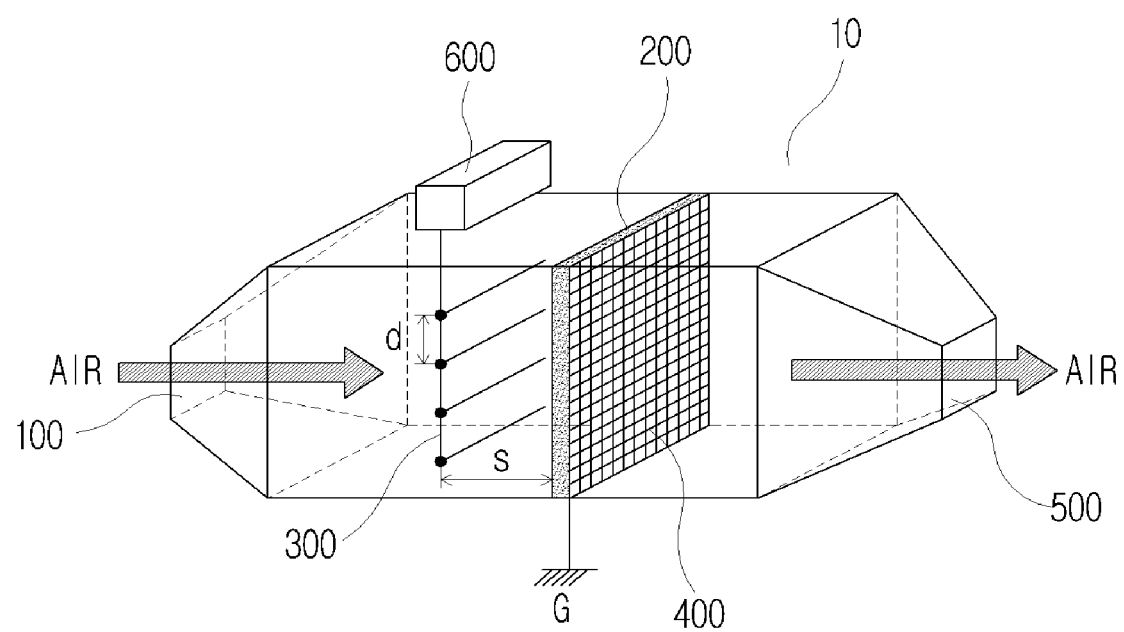
FIG. 1 is a configuration diagram of an indoor air cleaning device for a vehicle using a nonthermal plasma according to an embodiment of the present disclosure.

Hereinafter, the present disclosure is described in more detail with reference to the accompanying drawings. It is noted that in the drawings, like reference numerals denote like elements throughout as far as possible. Meanwhile, prior to the description, it should be understood that the terms or words used in the specification and the appended claims should not be construed as limited to general and dictionary meanings, but interpreted based on the meanings and concepts corresponding to the technical spirit of the present disclosure on the basis of the principle that the inventor is allowed to define terms appropriately for the best explanation. Therefore, the embodiments described herein and illustrations shown in the drawings are just a most preferred embodiment of the present disclosure, but not intended to fully describe the technical spirit of the present disclosure, and it should be understood that other equivalents and modifications could be made thereto at the time the application was filed.

FIG. 1 is a configuration diagram of an indoor air cleaning device 10 for a vehicle using a nonthermal plasma according to an embodiment of the present disclosure.

Referring to FIG. 1, the indoor air cleaning device 10 for a vehicle using a nonthermal plasma according to an embodiment of the present disclosure may include an air inlet unit 100, a filter unit 200, a discharge electrode unit 300, an inductive electrode unit 400, an air outlet unit 500 and a power control unit 600.

Describing the indoor air cleaning device 10 for a vehicle according to the present disclosure on the whole, the basic operation structure of air purification and circulation is that air from inside and outside enters the vehicle through the air inlet unit 100, infiltrated air is purified while passing through the filter unit 200 including an electrostatic filter, and purified air is discharged into the vehicle through the air outlet.

Here, the greatest feature of the present disclosure is that the discharge electrode unit 300 is formed on the front surface of the filter unit 200 and the inductive electrode unit 400 is formed on the rear surface of the filter unit 200, and when voltage is applied from the power control unit 600, discharge occurs, generating ozone, and the filter unit 200 is sterilized by the generated ozone.

Prior to the detailed description of the structure of the electrode unit, a sterilization method of an air purifying filter, for example, an electrostatic filter will be summarized in brief. In general, a bacteria sterilization method of a filter for indoor air purification includes a radiation method (UV method), a gas method and an electric discharge method, and among them, a sterilization method using ozone ($O_3$) generated by a nonthermal plasma through electric discharge uses the strong oxidizing action of ozone.

Because ozone generated by a nonthermal discharge plasma has the strong oxidizing power and is reduced to oxygen in a short time, an advantage is that it does not generate residual pollutants, and thus it is used in a wide variety of applications in the industry, for example, air pollutant removal, water purification, sterilization and deodoration. In the case of ozone sterilization, it is generally used for sterilization of commonly found bacteria such as *E. coli, B. subtilis* and *staphylococcus*.

Ozone has the strongest oxidizing power after fluorine, and due to the oxidizing power, ozone has the properties of sterilization, deodoration, decoloration, and reaction with organics and inorganics. The sterilization power of ozone is strong enough to kill most of bacteria, virus and molds for 4 minutes at the ozone concentration of 0.4 ppm. At higher concentrations, the sterilization power of ozone greatly increases, and it is so powerful enough to break the cell wall in a few seconds, resulting in degradation of cytoplasm which is impossible to be regenerated. In addition, ozone has a great effect of removing odors.

So far, studies have been made on ozone generators using various methods including dielectric barrier discharge, potential discharge, pulsed corona discharge, surface discharge, silent discharge and glow discharge, and among them, the corona discharge method is known as a method that has the simplest structure and efficiently generates ozone by forming a strong non-uniform electric field. Accordingly, the indoor air cleaning device 10 for a vehicle using a nonthermal plasma according to an embodiment of the present disclosure is characterized in that discharge by the discharge electrode unit 300 and the inductive electrode unit 400 is a corona discharge by a non-uniform electric field.

More specifically, in an embodiment of the present disclosure, the discharge electrode unit 300 may include one or more wire electrodes made of stainless steel. The wire electrode made of stainless steel 402, about 0.2 mm in diameter and about 230 mm in length may be used, and in the case of a plurality of wire electrodes, each wire electrode should be installed at the same distanced.

Additionally, in the present disclosure, the inductive electrode unit 400 preferably includes a mesh electrode made of stainless steel. The filter unit 200 is interposed between the wire electrode and the mesh electrode, and in this instance, the discharge electrode unit 300 and the inductive electrode unit 400 are preferably installed at spacings of 22 to 26 mm.

Corona discharge is brought on by a non-uniform electric field between the discharge electrode unit 300 including the wire electrode and the inductive electrode unit 400 including the mesh electrode, generating ozone. To generate enhanced corona discharge, preferably the number of wire electrodes does not exceed a maximum of seven wire electrodes so that the distance between each wire electrode is sufficiently larger than the spacings between the discharge electrode unit 300 and the inductive electrode unit 400.

Under the same applied voltage, as the number of wire electrodes increases, an amount of generated ozone increases, too. In fact, because ozone of low concentration as much as about 2 ppm is sufficient to sterilize the electrostatic filter of the filter unit 200, it does not matter that only one wire electrode is used for sterilization, and rather it is good in terms of power efficiency. However, to use surface discharge generated from the filter of the filter unit 200 together with sterilization, a larger number of wire electrodes is needed to cause surface discharge over the wide area.

Describing the mechanism of corona discharge taking place in the present disclosure, when direct current high voltage is applied to the wire electrode of the discharge electrode unit 300 through the power control unit 600, the discharge current rapidly increases after corona discharge initiation voltage, and when voltage above dielectric breakdown voltage is applied, corona discharge characteristics leading to dielectric breakdown are exhibited. After corona discharge occurs near the wire electrode by a non-uniform electric field, when the applied voltage further increases, ions generated by corona discharge are sufficiently accumulated on the filter of the filter unit 200.

After that, the accumulated ions move to the inductive electrode unit through pores of the filter unit 200, causing surface discharge. That is, the present disclosure may generate ozone not only by the discharge of the two electrode units but also by the surface discharge on the filter unit 200, resulting in a further increase in ozone generation efficiency.

Figure 2A:
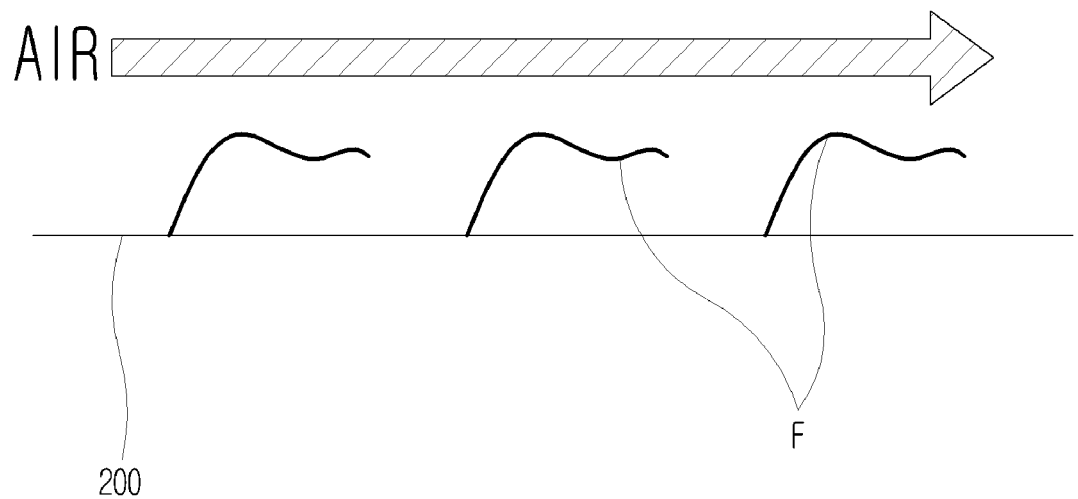
FIG. 2A is a diagram showing reduced static electricity in fibers of a filter unit in an indoor air cleaning device for a vehicle using a nonthermal plasma according to an embodiment of the present disclosure.
Figure 2B:
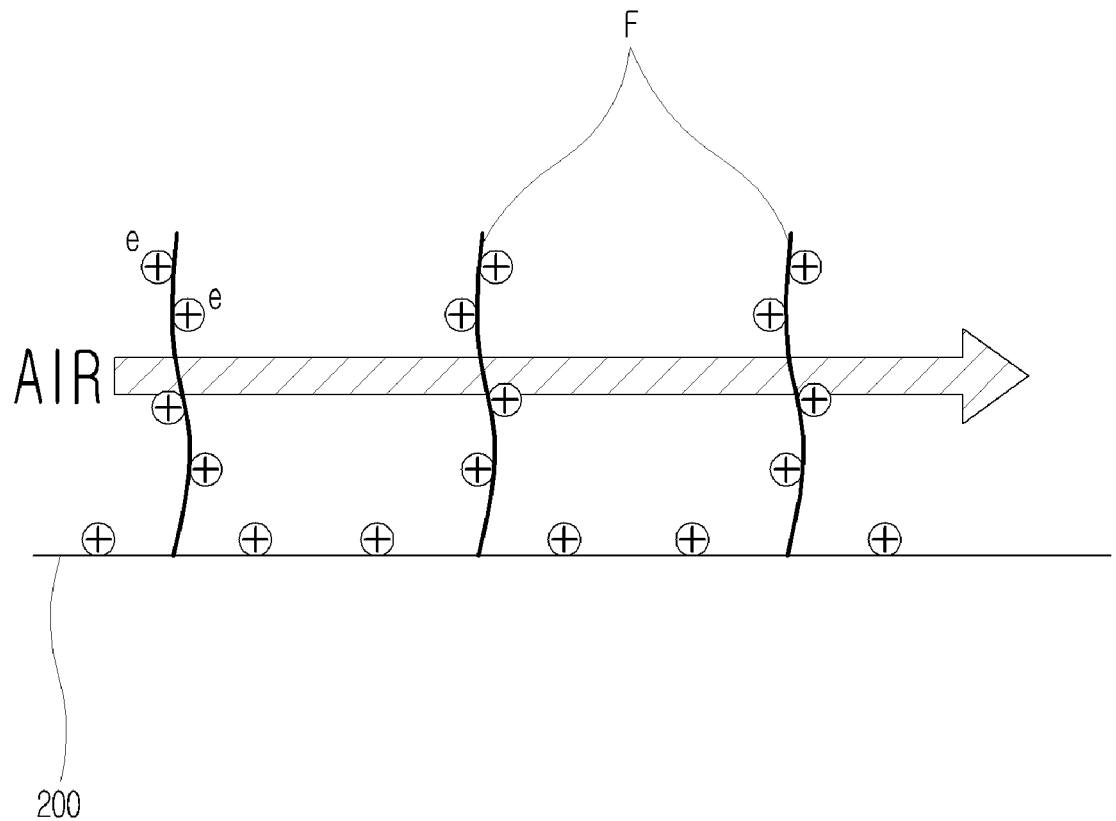
FIG. 2B is a diagram showing static electricity charged in fibers of a filter unit through an electrostatic charging mode in an indoor air cleaning device for a vehicle using a nonthermal plasma according to an embodiment of the present disclosure.

FIG. 2A is a diagram showing reduced static electricity in the fibers of the filter unit 200 in the indoor air cleaning device 10 for a vehicle using a nonthermal plasma according to an embodiment of the present disclosure, and FIG. 2B is a diagram showing static electricity charged in the fibers of the filter unit 200 through an electrostatic charging mode in the indoor air cleaning device 10 for a vehicle using a nonthermal plasma according to an embodiment of the present disclosure.

Referring to FIG. 2, the indoor air cleaning device 10 for a vehicle using a nonthermal plasma according to an embodiment of the present disclosure may charge static electricity in the filter fibers of the filter unit 200.

First, the indoor air cleaning device 10 for a vehicle using a nonthermal plasma according to the present disclosure preferably allows a user to adjust the magnitude of voltage applied to the discharge electrode unit 300 and the inductive electrode unit 400 by the power control unit 600. It is possible to operate stepwise in an electrostatic charging mode, a negative ion generation mode and an ozone sterilization mode according to the magnitude of voltage adjusted by the power control unit 600. To allow the user to adjust the magnitude of voltage, it will be preferred that a mode selection button (not shown) operates with manipulation buttons of the vehicle to allow the user to easily manipulate.

As the electrostatic filter used in the filter unit 200 is exposed to the outside for a long term, the surface area of the filter is reduced due to a reduction of static charge electrically charged in the filter and agglomeration phenomena of the filter fibers as shown in FIG. 2A, and accordingly, the filter effect is drastically reduced. In this instance, when magnitude of voltage which is lower than that enough to generate ozone is applied from the power control unit 600, an electrostatic force may be given to the filter, making the filter fibers extend in all directions as shown in FIG. 2B. That is, an increase in the surface area of the filter fibers prevents the reduction in microparticle capturing capability of the filter unit 200.

The indoor air cleaning device 10 for a vehicle using a nonthermal plasma according to an embodiment of the present disclosure may maintain the best purification performance of the filter unit 200 by periodically using the electrostatic charging mode. Further to this, when the applied voltage further increases to reach the negative ion generation mode, negative ions beneficial for human body are generated, inducing a pleasant indoor environment.

In the ozone sterilization mode in which the highest voltage is applied, ozone sterilization of the filter unit 200 is performed as described above. That is, the indoor air cleaning device 10 for a vehicle using a nonthermal plasma according to the present disclosure may efficiently sterilize the air purifying filter in combination with the corona discharge method of simple structure, recharge static elasticity of the electrostatic filter with the precisely controlled magnitude of the applied voltage to maintain the best purification performance of the filter, and generate negative ions beneficial for human body, creating pleasant indoor air conditions.

In another embodiment of the present disclosure, a nonthermal plasma generator including the discharge electrode unit 300 and the inductive electrode unit 400 may operate with the fan attached to the air conditioner in the vehicle, so when the air conditioner operates, it always automatically operates, and at other times, it stops operating, to avoid unnecessary power consumption.

Additionally, if there is ozone remaining in air having passed the indoor air cleaning device 10 for a vehicle, the ozone is harmful to human body upon entering the vehicle, and thus means for removing the residual ozone is necessary, and to this end, an ozone removing unit may be separately provided in the air outlet unit 500. The ozone removing unit may be installed by combining carbon with good ozone adsorption and a separate filter.

Further, an air flow path may be extended to discharge ozone generated from the indoor air cleaning device 10 for a vehicle according to the present disclosure from the air outlet unit 500 to each interior part of the vehicle, in order to remove bad odors in the filter unit 200 as well as the inside of the vehicle and sterilize even the car seats and interior accessories. In a rainy season or wet environment, the indoor air cleaning treatment through ozone may provide a pleasant driving environment to the driver. Of course, to avoid the direct effects of ozone on human body, it is required to operate when the driver is not in the vehicle. For example, it will be desirable to execute this function when the vehicle is parked at night, and to this end, a timer function may be added.

While the present disclosure has been described with regard to the above-mentioned preferred embodiments, various changes or modifications may be made thereto without departing from the spirit and scope of the present disclosure. Therefore, the scope of the appended claims will cover such changes or modification within the spirit of the present disclosure.

The invention claimed is:
1. An operation method of an indoor air cleaning device which is to be installed inside a vehicle, the indoor air cleaning device comprising:
an air inlet through which air is to be introduced;
an electrostatic filter configured to purify the air;

a discharge electrode disposed on or over a front surface of the electrostatic filter and including two or more wire electrodes;

an inductive electrode disposed on a rear surface of the electrostatic filter and including a mesh electrode;

an air outlet through which the air purified by the electrostatic filter is to be discharged to inside the vehicle;

an ozone removing assembly disposed in the air outlet to remove residual ozone inside the vehicle; and a power control assembly configured to apply a voltage to the discharge electrode and the inductive electrode, the operation method comprising:

performing an ozone sterilization mode, in which a first voltage is applied to the discharge electrode, such that a corona discharge occurs between the discharge electrode and the inductive electrode by a non-uniform electric field, wherein, by increasing the first voltage applied to the discharge electrode, ions generated by the corona discharge are accumulated on the electrostatic filter, and the accumulated ions move to the inductive electrode through pores of the electrostatic filter and cause surface discharge, by which ozone is generated;

performing an electrostatic charging mode, in which a second voltage is periodically applied to the electrostatic filter to electrostatically recharge the electrostatic filter, wherein the second voltage is lower than the first voltage so as to be insufficient to generate the ozone;

performing a negative ion generation mode, in which a third voltage is applied to the electrostatic filter to generate negative ion, wherein the third voltage is higher than the second voltage so as to be sufficient to generate the negative ion and insufficient to generate the ozone; and performing an extended ozone discharging mode, in which an air flow path is extended from the air outlet to an interior of the vehicle to discharge ozone generated in the indoor air cleaning device to the interior of the vehicle, wherein the performing the ozone discharging mode is executed only when the vehicle is parked in a predetermined period as set by a timer.

2. The operation method of the indoor air cleaning device of claim 1, wherein electrodes of the discharge electrode and the inductive electrode are made of stainless steel.

3. The operation method of the indoor air cleaning device of claim 1, wherein the discharge electrode includes no more than seven wire electrodes.

4. The operation method of the indoor air cleaning device of claim 1, wherein the discharge electrode and the inductive electrode are disposed at a spacing of 22 to 26 mm.

5. The operation method of the indoor air cleaning device of claim 1, wherein each of the electrostatic charging mode, the negative ion generation mode, and the ozone sterilization mode is performed in reply to a magnitude of voltage adjusted by the power control assembly.

6. The operation method of the indoor air cleaning device of claim 5, wherein the indoor air cleaning device further comprises a mode selection button configured to adjust the magnitude of voltage.

* * * * *